(12) United States Patent
Knudsen et al.

(10) Patent No.: US 11,850,434 B2
(45) Date of Patent: Dec. 26, 2023

(54) SYSTEM FOR ELECTRICAL STIMULATION OF NERVES

(71) Applicant: INNOCON MEDICAL APS, Aalborg (DK)

(72) Inventors: Dianna Maersk Knudsen, Logstor (DK); Torsten Fjeldgaard Hvalsoe, Aalborg (DK); Jesper Nielsen, Klarup (DK)

(73) Assignee: INNOCON MEDICAL APS, Aalborg (DK)

( * ) Notice: Subject to any disclaimer, the term of this patent is extended or adjusted under 35 U.S.C. 154(b) by 0 days.

(21) Appl. No.: 16/640,042

(22) PCT Filed: Aug. 19, 2018

(86) PCT No.: PCT/DK2018/050200
§ 371 (c)(1),
(2) Date: Feb. 18, 2020

(87) PCT Pub. No.: WO2019/034223
PCT Pub. Date: Feb. 21, 2019

(65) Prior Publication Data
US 2020/0222706 A1  Jul. 16, 2020

(30) Foreign Application Priority Data

Aug. 18, 2017 (DK) .............................. PA201700045
Feb. 8, 2018 (DK) .............................. PA201800060

(51) Int. Cl.
*A61N 1/05* (2006.01)
*A61N 1/375* (2006.01)
(Continued)

(52) U.S. Cl.
CPC ....... *A61N 1/37518* (2017.08); *A61N 1/0456* (2013.01); *A61N 1/0504* (2013.01); *A61N 1/0521* (2013.01); *A61N 1/0558* (2013.01); *A61N 1/36007* (2013.01); *A61N 1/36057* (2013.01)

(58) Field of Classification Search
CPC .............. A61N 1/37518; A61N 1/0456; A61N 1/0504; A61N 1/0558
See application file for complete search history.

(56) References Cited

U.S. PATENT DOCUMENTS 5,144,952 A * 9/1992 Frachet .................... A61N 1/05
600/379
9,101,277 B2 * 8/2015 Doerr ................... A61N 1/0504
(Continued)

FOREIGN PATENT DOCUMENTS

JP   2010-505550 A   10/2013
WO  2012139063 A2   10/2012
(Continued)

*Primary Examiner* — Eric D. Bertram
(74) *Attorney, Agent, or Firm* — HOLLAND & HART LLP

(57) ABSTRACT

A system for electrical stimulation of nerves of a living being, including a pulse generator configured to provide a sequence of electrical pulses to at least one electrode that are maintained in close proximity to the nerve of interest with the use of a feature to secure the electrode to the skin or tissue of the living being.

20 Claims, 3 Drawing Sheets

(51) Int. Cl.
*A61N 1/04* (2006.01)
*A61N 1/36* (2006.01)

(56) References Cited

U.S. PATENT DOCUMENTS

2012/0035451 A1 2/2012 Jaffe
2015/0126846 A1 5/2015 Jia
2015/0352357 A1 12/2015 Wei

FOREIGN PATENT DOCUMENTS

WO 2017011305 A1 1/2017
WO 2019034223 A1 2/2019

* cited by examiner

SYSTEM FOR ELECTRICAL STIMULATION OF NERVES

CROSS REFERENCE TO RELATED APPLICATIONS

This application is a U.S. National Entry and claims priority to PCT International Patent Application No. PCT/DK2018/050200, filed 19 Aug. 2018, and entitled "SYSTEM FOR ELECRICAL STIMULATION OF NERVES", which claims priority to Denmark Patent Applications No. PA201700045 filed 8 Feb. 2018, and No. PA201800060 filed 18 Aug. 2017, the entire disclosures of which are incorporated herein by this reference.

TECHNICAL FIELD

The present invention is generally concerned with electrical stimulation of nerves.

BACKGROUND

Stimulation of nerves is known to have a positive effect on a variety of illnesses that derives from a defective nervous system. Electrical stimulation of the vagus nerve has as an example proven to be an efficacious treatment of epilepsy. It has also been shown that stimulation of the genital nerves can have a positive effect in the treatment of fecal and urinary incontinence.

For the sake of explaining the invention, the treatment of incontinence has been chosen to exemplify the advantageous features but should not be taken as limiting for the scope of the invention for which the inventive concept could be carried out in order to stimulate nerves contained in the human body without specifying the reason for stimulating the specific nerve.

Overactive bladder (OAB) syndrome is a highly prevalent condition worldwide, particularly in the general population above 40 years, where prevalence has been reported to be about 17%. Frequency (85%) is the most commonly reported symptom, followed by urgency (54%) and urge urinary incontinence (36%). These symptoms adversely affect patients' quality of life due to social and hygienic difficulties. Upper urinary tract damage caused by sustained high intravesical pressures and repeated bladder infections is another concern that causes morbidity, hospitalization or even death. Conventional treatment is typically based on drugs with dose-limiting systemic side effects.

Fecal incontinence (FI) is also highly frequent with prevalence between 5-15% in the general population. It is commonly defined as the involuntary loss of solid or liquid feces or mucus and is a disabling symptom, which can have a devastating impact on quality of life, as its effects may include embarrassment, social isolation, and even loss of employment. Conservative treatment may be dietetic measures, various pharmacological agents, anorectal rehabilitation, and transanal irrigation.

In both OAB and FI surgical destructive interventions may be considered if patients are refractory to conventional treatment options but complication rates are often high. Alternative treatment options should be considered in refractory patients to avoid destructive surgery.

Continuous or intermittent electrical stimulation of the sacral nerves is known to be effective in the treatment of a variety of pelvic disorders, such as OAB and FI (InterStim® Therapy, Medtronic, MN, USA). InterStim® Therapy is based on electrical stimulation of the sacral root/s using a medical lead connected to an implanted pulse generator. The pulse generator is programmable by means of an external control device via wireless data transmission. Electrical stimulation of the sacral root/s activates sacral somatic afferents that modulate the sacral reflex pathways. This effect is also known as neuromodulation and has been shown to reduce the symptoms of OAB and FI.

However, an implantable system is quite expensive in hardware costs and for the act of implanting the system into the living being. Additionally, implanting a medical system into a living being should only be offered if all alternative solutions available have failed. There seems to be a need for a simpler and cheaper solution that provides an acceptable solution to the outlined problem without the need for an implanted system.

US 2015/0352357 A1 to Medtronic present a solution providing a surface electrode in two variants. One for male use and one for female use, each variant designed in attempt to take advantage of the specific shape of the genitals of the genders and attempting to arrange electrodes that target the genital nerves. However, the disclosure does not explain how the electrodes are arranged and secured in a desired position where an effective electrical charge can be addressed towards the genital nerves.

Typically, surface electrodes are patch type electrodes utilizing an adhesive and conductive hydrogel, with various supportive scrims and fabrics for strength and structural support. Due to the necessity of supportive scrims and wire meshes most types of such electrodes becomes relatively stiff and rigid. This has the effect that the electrodes looseness from the skin to which they are applied, especially during activity, or when applied to uneven structures such as the genitals or the Achilles tendon, leading to loss of functionality.

Thus, there is a need for an improvement that provides a stable electrode interface towards the genital nerves and provides a secure arrangement on the skin of the human being on the position of interest in close proximity to the genital nerves.

SUMMARY

It is an object of the embodiments of the present invention to provide a system, which overcomes or at least reduces the above-mentioned disadvantages.

The present invention provides a solution, where the electrode is secured and kept in the same distance and with the same orientation with regard to the position of the part of the nerve and/or its branches decided to be treated, thus the electrode and the nerve being positioned mutually in the same stable position with regard to each other.

For a surface stimulation system for stimulating the dorsal genital nerves, the challenges of fixation are considerably higher than for the standard surface stimulation systems on the market. Fixation near or at the genitals require solutions targeted both female and male users due to the natural anatomical differences. Additionally, to gender variations, individual variations are challenging. The nerves to be targeted are the dorsal genital nerves (clitoris/penile nerves), which are possible to access with surface electrodes using suitable stimulation. The target area is the genital region i.e. along the penis and in close proximity of the clitoris.

The challenge of having naked skin in the genital region is most considerable for female users, and may require some intimate shaving for many users. This is known to create skin irritation and itching, and is thus likely uncomfortable for many users.

The ground, anode or return electrode may be positioned in close proximity of the cathode electrode or stimulating electrode, or distant. The latter may provide an option for a relative larger electrode, thus eliminating many of the issues to be addressed for the cathode electrode. Male users may have body hair covering most of the abdomen and may therefore prefer bi-polar designs rather than larger return patch electrodes.

The application may require either quick-onset of the stimulation if/when requested, continuous stimulation during day and/or night, including periodic therapy sessions, depending of the clinically supported setup for the specific patient/user. Thus, the reliability of the fixation is of crucial importance for the product, and may be a different use scenario compared to many other applications. An important aspect is the freedom of movement required during everyday activities such as walking, biking, running or other sports related activities, even further stressing out the critical importance of reliable and comfortable fixation of electrode/s.

More specifically, fixation of neuromodulation electrodes for methods to treat pelvic floor disorders, such as urinary and fecal incontinence, by stimulation of the left and/or right branches of the dorsal genital nerves, or pudendal nerve afferents, is according to the present invention implemented using an electrode fixation unit inserted through the cutaneous tissue in the region along the penis, and/or at or near the glans of the clitoris, in close proximity of the targeted nerve/s, to support the arrangement of neuromodulation electrodes.

The intended level of fixation shall prevent the electrodes to dislocate from the site in the tissue intended to be stimulated. It is not intended to be fully anchored or grown in, i.e. it shall remain possible to be removed without clinical intervention.

In males the dorsal genital nerve is superficial on the dorsal side (i.e. at approximately the upper ¼ of the cross section of the penis), and runs along the length of the shaft of the penis until it reaches the glans, where it fans out.

In females the dorsal genital nerves tend to be close to the mucous membrane (or skin) near the glans of the clitoris between the labium minus and labium majus. Thus, these sites of stimulation are effective for both males and females, since factors such as fat layer and muscle tissue have a significant influence on the activation of the targeted nerves. At the intended site of stimulation, the fat layer is limited, and no muscles cover the nerves.

A reliable means of fixation in the tissue is presented by use of an electrode fixation unit, which is arranged in a formed channel in and out of the skin at the targeted tissue to be stimulated. In general, the disclosure is directed to fixation means of piercing the skin to fixate electrodes for delivering of electrical stimulation. In one embodiment, the disclosure is directed to fixation of surface electrodes by use of a pierced element in combination with a patch, pad or similar type of surface electrode, whether configured with a lead or an arrangement for attaching a lead, such as a typical snap connector. In a further embodiment, the disclosure is directed to be part of the signal pathway, providing fixation and signal to surface electrodes through means of a lead connected to the pierced element having multiple freedom of movement.

The invention is explained using a variant of the inventive electrode system for treating incontinence, but it has to be understood that the concept can be used on the entire body where access to nerves underlying the skin is targeted electrical stimulation. It could be on the neck for treating epilepsy or it could be on the extremities for treating other nervous system impairments.

In a first aspect, the invention provides a system for electrical stimulation of nerves of a living being, including a system for electrical stimulation of nerves of a living being, including an electrode fixation unit configured to be placed in a superficially formed channel in the skin, and specially adapted for providing suitable fixation of at least one electrode configured to be placed in close proximity of a portion of a nerve of a living being for electrical stimulation of nerves, and a pulse generator configured to provide a sequence of electrical pulses to the at least one electrode in order to achieve electrical stimulation of the nerve, where the electrode fixation unit has a first end and a second end, where the first end of the electrode fixation unit is configured to protrude out of the first end of the formed channel and the second end of the electrode fixation unit is configured to protrude out of the second end of the formed channel and where an electrode fixation unit body member is forming the structure of the electrode fixation unit, the electrode fixation unit body constituting the fixation member onto which the at least one electrode is arranged or included, and where at least one end termination member, configured to be repeatedly non-destructively dismantled from and reassembled to the electrode fixation unit body, is configured to provide a stop for movement of the electrode fixation unit body in at least one direction within the formed channel, where the at least one end termination is positioned outside the first and/or second end of the formed channel, providing a mechanically interlocking mechanism by means of geometry of the end termination for the electrode fixation unit when the electrode fixation unit is arranged in the formed channel.

More expediently, the electrode fixation unit has an elongated form the electrode fixation unit having a first end and a second end where the first end of the electrode fixation unit body is configured to protrude out of the superficially formed channel in the skin through a first perforation of the skin and the second end are configured to protrude out of a second perforation of the skin of the superficially formed channel in the skin formed by two interconnected perforations of the skin of a living being when said electrode fixation unit is inserted into said formed channel.

In an embodiment, the at least one end termination member is arranged on the electrode fixation unit body as a hinge or ductile formable structure member.

In an embodiment, the at least one end termination member is attached to form closure of the electrode fixation unit body into a closed loop, a geometrically closing or an overlapping structure.

In an embodiment, the at least one end termination member is attached to an end of the electrode fixation unit body but with a gap between the end termination member and the other end of the electrode fixation unit body featuring or not featuring another end termination member. It has to be understood that fixation in the skin does not rely on forming a completely closed loop but on a maintaining a safe fixation which will also be the case even if there is formed a gap.

In an embodiment, the electrode fixation unit is configured to repeatedly be non-destructively dismantled into at least two elements and reassembled, once arranged in the formed channel.

In an embodiment, the electrode fixation unit body is solid-, hollow- or tubular-formed and the cross section is having a triangular, squared or multiple angled cross section until substantially being circular or elliptical formed with even or uneven sized sides and/or with straight or curved sides and where the electrode fixation unit in the longitudinal direction can travel in a straight or bended or curved or spiral or meandering or a combination of said travel form directions.

However, in embodiments of the invention, the shape of the electrode fixation unit vary with straight or shaped electrode fixation unit bodies to complete enclosing rings of various designs and sizes. Appreciated configurations of electrode fixation units tailor made to the preference and needs of the individual user have cross sections ranging from a diameter of one millimeter to ten millimeters with a typical shaft length in the range of ten to forty millimeters. The curvature of the fixation unit can vary relative to the tissue variation or personal preferences from straight to complete enclosed designs and the said curvature need not be constant.

In a number of embodiments, the electrode fixation unit comprises a biocompatible electrical conductible material such as titanium, medical grade stainless steel, platinum, platinum/iridium, medical grade metals and other precious metal alloys suitable for electrical stimulation and/or comprises a biocompatible electrical isolating material such as silicone, polyurethane, ceramics, PTFE or PEEK and/or comprises a flexible or resilient material.

However, to be more specific, examples of various materials for the electrode fixation unit and for the later in the description explained patch member include biocompatible thermoplastic materials such as Polyether-ketone based materials, HD-PE, PP, PET, Fluorinated polymer materials, or other sterilizable materials suitable for permanent contact through the skin of the patient. A metal based version of a fixation unit could be made from surgical steel like 316 LVM, titanium based alloys and precious metal alloys. Additionally, ceramics may be used for shorter lengths and/or larger diameters of the electrode fixation unit body. In an embodiment the fixation unit or the electrode are coated with precious metal alloys, titanium nitride or diamond like carbon in order to achieve better conductibility with high biocompatibility. In an embodiment, the coating constitutes a means for adjustment of the impedance at the skin/electrode interface.

In an embodiment, the at least one of the first or second ends of said electrode fixation unit are configured with a part which forms a stop for moving the electrode fixation unit through the formed channel in the tissue in one direction. When the system is not activated the lead providing the stimulating signal can be removed entirely to allow the user to have maximum freedom from relevant inconveniences.

Inserted into the tissue, the electrode fixation unit forms a stable fixation mechanism for having a fixed position specifying a fixed distance to the nerve of interest. Thus, the electrode fixation unit serves as a stable platform for arranging one or more electrodes for submitting a neuromodulation signal addressed to the nerve of interest. For securing the electrode fixation unit in the fixed position in the formed channel at least one end termination on the electrode fixation unit is provided to avoid that electrode the fixation unit can move out of the formed channel in the tissue. When inserted into the formed channel an end termination can be provided in the end not initially being equipped with an end termination. The end termination can be provided in various ways.

It has to be understood that the end termination can be formed in various ways almost without any limits. However, considerations to the design need to address risks of infections if such would result in end termination designs that are difficult to maintain hygienically. Too pointy shapes and details may thus not be suitable as end termination.

In one embodiment, the end termination is formed by configuring the end of the electrode fixation unit at least on a part of the first or the second end that is configured to protrude out of the formed channel with a cross-section that is larger than the measured circumscribed cross-section of the formed channel in such a way as to form a stop for movement of the electrode fixation unit through the formed channel in one direction.

In a further embodiment, the end termination is formed by configuring the end of the fixation unit at least on a part of the first or the second end that is configured to protrude out of the formed channel with a thread for receiving a nut, said nut having a cross-section that is sufficiently larger than the measured cross-section of the formed channel in such a way as to form a stop for movement of the electrode fixation unit through the formed channel in one direction. In an embodiment, the stop is provided by adding an end termination by snapping it on the electrode fixation unit body. Since the electrode fixation unit body may need to be removed for care of the skin and the formed channel and/or for hygienically maintenance the electrode fixation unit body, it should be possible to remove the end termination or dismantle the electrode fixation unit body between the end terminations to allow an easy way in order to remove the electrode fixation unit out of the formed channel in the tissue, without the need for clinical intervention.

The attachment of the end termination can include click-in features involving a spring member, or a magnet member, thread or similar interface between the electrode fixation unit body and the end termination.

The end terminations to be arranged on the electrode fixation unit body ends can be designed in various ways, where one or all end terminations can be exchanged or interchanged to the preference of the wearer, to match for instances the skin or tissue color.

In one embodiment, the electrode fixation unit is designed to have two exchangeable end terminations of various designs for the preference of the wearer. The electrode fixation unit has two corresponding features of various designs to allow attachment of the electrode into or onto the electrode fixation unit. In embodiments, the end terminations are be threaded internally or have an external thread that allow exchange. Other forms of attachment include click-in features involving a spring feature, or a magnet interface between the electrode fixation unit body and the end termination.

In an embodiment, an end of the electrode fixation unit, at least on a part of the first and/or the second end that is configured to protrude out of the formed channel is configured with an interface for receiving a detachable end termination, the end termination being attached and secured in position by means of spring-loaded or magnetic force or click-in or by a threaded connection. Alternatively, the electrode fixation unit shall allow to be dismantled in some position on the electrode fixation unit body.

In yet another embodiment, the electrode fixation unit constitutes the at least one electrode. In the most simple embodiment, the electrode fixation unit is electrical conductible all over and serves as an electrode itself and is configured to provide electrical stimulation from the entire surface of the electrode fixation unit at the surface where it is in contact with tissue.

In more sophisticated embodiments, the electrode fixation unit body is partly made of an electrical isolating material and having electrical conductible sections which serve as electrodes. In an embodiment, the electrodes are each forming independent poles supplied by different nerve stimulation signals or supplied from the same electrical stimulation pattern source or serving as anodes and cathodes. In an embodiment the electrode fixation unit body is hollow and the electrical connection/s to the electrode/s are running inside the device and terminated in a connector accessible from outside the electrode fixation unit. A monopolar electrode device can be provided in this way but also bipolar or multipolar electrode devices.

In another embodiment, the at least one electrode is arranged on the electrode fixation unit. In an embodiment, the at least one electrode are arranged with one of the end terminations. In another embodiment, it is simply attached to the electrode fixation unit.

In a further embodiment, the electrode fixation unit, with or without attached end terminations, forms an electrical isolating part where the at least one electrode or multiple electrodes are arranged on or in the electrode fixation unit in a position where the electrode fixation unit is adapted to be in contact with the skin inside or outside the formed channel in the skin/tissue.

In an embodiment, the at least one end termination comprises electrically isolating materials, such as PEEK, fluorinated materials, ceramics or similar materials.

In another embodiment, the at least one end termination constitutes an electrical stimulating electrode utilizing suitable conductive materials.

In an embodiment, the electrode fixation unit comprises at least one detachable electrical connection providing the stimulation signal from a pulse generator to the at least one applied electrode.

In an embodiment, the system comprises a patch member, and where each of the first and/or the second ends of the electrode fixation unit are adapted to form anchoring points for connecting and/or securing said patch member in position on the skin where the patch member is forming a bridge between said first and second ends of the electrode fixation unit.

In yet another embodiment, the electrode fixation unit comprises a patch member where at least one of the first and/or the second ends of the electrode fixation unit are adapted to form at least one point for connecting and supporting said patch member in position on the skin, or where the patch member is forming a bridge between said first and second ends of the fixation unit.

The patch member is in one embodiment secured by the means of the end terminations. In an embodiment, the patch member arranges the electrode fixation unit in a spring biased or elastic position kept in place by the two end terminations of the electrode fixation unit. In an embodiment, the attachment of the patch member is made through penetrated holes in the patch member or carved out on the edge of said patch member. For the understanding, the patch member can be substantially flat and extending in a way that covers the end terminations of the electrode fixation unit or just reaches out to be connected with the electrode fixation unit and extends thereto. In an embodiment, the patch member is circular shaped. In another embodiment, the patch member is oval shaped. It has to be understood that the patch members can be configured with a shape that serves to provide the best platform for arranging the electrode/s, the pulse generator or interface so no particular shape should be excluded. In yet another embodiment the extent of the patch member provides the space for attachment to the skin of the user in at least one further position or at multiple positions.

In an embodiment, the patch member is attached to at least one of or only one of the first or the second end of the electrode fixation unit. This facilitates a small physical size of the patch member where the end of the electrode fixation unit is adapted for securing the patch member in a stable position with regard to the nerve of interest.

In a special embodiment, which is appreciated, the electrode fixation unit forms an electrical isolating part with at least one electrical connection interface for providing a stimulation signal to an electrode and where the electrode is arranged on the electrode fixation unit in a position where the electrode fixation unit is adapted to be in contact with the skin. A simple device is provided which only needs a single attachment to a pulse generator.

In a further embodiment, the bridge like patch member is adapted for holding the electrode. It has to be understood that the electrode should be arranged on the patch member on the face that is towards the skin. In an embodiment, the electrode is arranged in a standard position on the patch member or arranged after determining the best position on the patch member. In an embodiment, multiple electrodes are arranged on the patch member.

In an embodiment, the bridge like patch member has two penetrations specially adapted for receiving the first end and the second end of the electrode fixation unit and where the end terminations on the electrode fixation unit forms stops for keeping the patch in position on situ on the skin (forms a bracket or clasp).

In an embodiment, the bridge-like patch member has further penetrations specially adapted for being connected to further electrode fixation units for securing the bridge like patch member to further positions on the skin.

In yet another embodiment, the electrode fixation unit facilitates a mechanism to connect with the electrode or the patch member. In embodiments, the mechanism means is one of magnetic, click-in, snap-hooks, snap connectors, etc. Thus, the electrode fixation unit and the arrangement in the formed channel in the tissue of the living being represents a new fixture for use with electrodes such as patch or pad electrodes or hydrogel-based electrodes that either have an attached lead included, or a snap connector to which the lead for the pulse generator can be attached.

In an appreciated embodiment, the system comprises an electrical connection between the electrode arranged on the electrode fixation unit or on the patch member and the pulse generator.

In various embodiments of the invention, the pulse generator is arranged in, on or with the electrode fixation unit or in, on or with a patch member.

In further embodiments, the pulse generator is connected to the electrode fixation unit via a detachable wired connection. The pulse generator is in an embodiment arranged remotely from the electrode fixation unit or the patch member.

In an embodiment, the system comprises a wired electrical connection between the at least one electrode and the pulse generator and comprises further a connector configured for releasing the wired electrical connection to the pulse generator when a preconfigured pull force is exceeded. The connection can be reobtained simply by re-connecting the wired connection to the electrode fixation unit. The socket is in an embodiment a plug and socket connector.

This is an appreciated behavior since pulling the electrode fixation unit in place in the formed channel can be harmful or painful to the user. Thus, a safety arrangement as explained will simply decouple the wire and protect the user from harm.

In an embodiment, the electrode is supported in situ in a spring retained arrangement in such a way that when a preconfigured pull force is exceeded on the wired connection, the electrode and/or the wire is released from its position on the electrode fixation unit or the patch member. This is another solution for protecting the user against pulling the electrode fixation unit in the formed channel.

It has to be understood that electrical stimulation will need a signal to be provided through a first electrode, which will return to the pulse generator via a second connection or electrode. Thus, the invention also comprises a second electrode that in embodiments are arranged on the electrode fixation unit, on the patch member or with the pulse generator serving as a counter electrode for the at least one electrode arranged on the electrode fixation unit or on the patch member.

Fixating the stimulation electrode in position on the skin by using an electrode fixation unit adapted to be inserted into a formed channel in the living being leaves out all considerations on migration issues. Electrode dislocation, in relation to the nerve of interest, has fatal consequences for the efficacy of the system. The establishment of a stable nerve electrode interface is of crucial importance for systems applying electrical stimulation of nerves in order to treat physical disorders.

BRIEF DESCRIPTION OF THE DRAWINGS

For the purpose of illustrating the invention, forms are shown in accompanying drawing, which are presently preferred, it being understood that the invention is not intended to be limited to the precise arrangements and instrumentalities shown. The invention includes.

DETAILED DESCRIPTION

Figure 1:
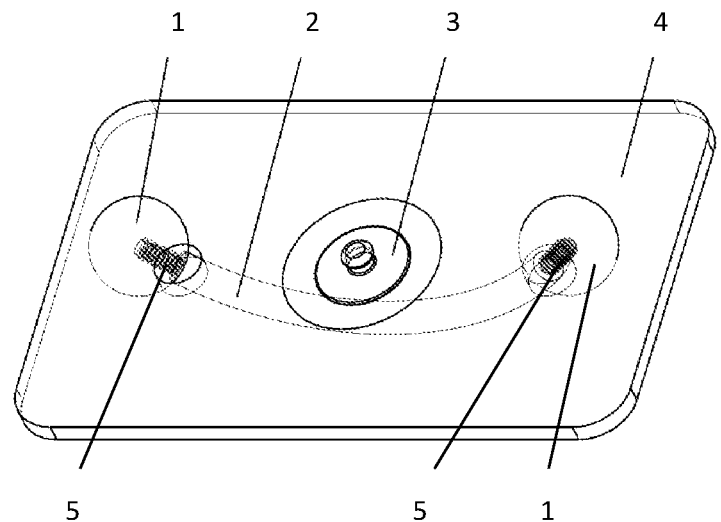
FIG. 1, which illustrates an electrode system comprising of an electrode fixation unit and a stimulating patch electrode.

FIG. 1, representing one embodiment of the electrode system, consists of a patch electrode (4) with a classical snap connector (3) supported by an electrode fixture element consisting of a bended electrode fixation unit body (2) with at least one detachable end termination (1) attached at the ends. The means for attachment of the end termination/s is threaded connections/s (5). It is crucial that the end terminations provide enough fixation force so that the patch member fixed to it does not loosen, or prevent the end terminations from falling off the electrode fixation unit body. The interlocking features of this system, prevents the patch electrode from loosening skin contact during use, even under conditions where large tissue movements are present. This shall however, be balanced with the convenience for the user, to easily detach the patch member or maintain the electrode fixation unit at wish, or exchange the electrode fixation unit if for any reason desired. Other electrode types can be attached to the electrode fixation unit, e.g. Ag/AgCl based electrodes, and further elements could be attached, such as a pulse generator, or any other parts of the applied system. The snap connector (3) is one means for connecting a lead to the pulse generator. Other electrically connectors are optional, such as jack-connectors or any other type, suitable for connection to a pulse generator. The geometrical surface area of the patch electrode is at least 25 mm2 and should be rounded to prevent sharp edges to irritate the tissue. The shape of the surface electrode is tailored to optimize the charge injection capacity and minimize edge effects. The electrode fixation unit body (2) can be resilient, made from polymers such as e.g. high durometer silicones, or relatively stiff, made from metals such as 316LVM, MP35N, ceramics or precious metals.

Figure 2:
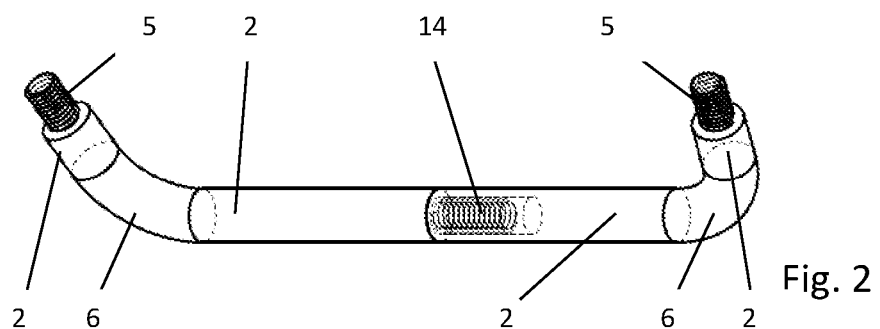
FIG. 2, illustrates one embodiment of a separable electrode fixation unit body, with threaded features also for end terminations to be attached.
Figure 3:
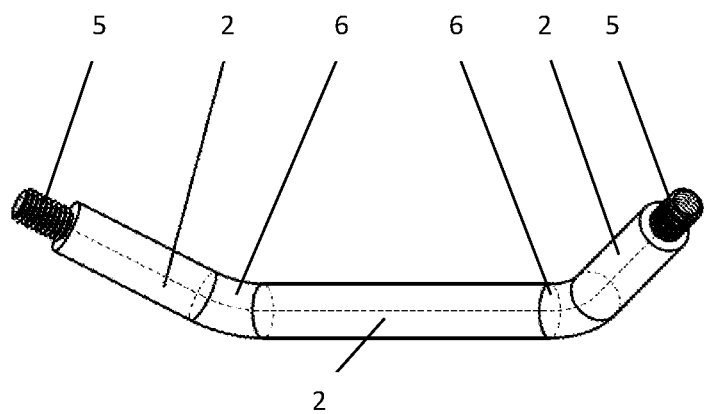
FIG. 3, illustrates one sharply bend embodiment of the electrode fixation unit body, with threaded features for end terminations to be attached.

FIGS. 2 and 3 represents an example of an electrode fixation unit body (2), where the method of end termination attachment is shown using threads (5). The electrode fixation unit body (2 and 6) can be solid as well as hollow. The electrode fixation unit body of FIG. 2 is separable and the joint (14), here exemplified as a threaded connection. The end terminations and the separable electrode fixation unit body could as well be clicked-in, magnetically attached, spring loaded or attached using similar concepts. The shape or design of the end terminations is preferably round and ball-shaped to be the least sharp as possible, and to allow easy hygienically maintenance and thus avoid infectious circumstances. Other designs are optional in some embodiments, especially when a patch electrode is included as part of the system, such as flat spade-shaped end terminations etc.

The shape of the electrode fixation unit body (2 and 6) can vary, having the goal to optimize the amount of tissue below the electrode fixation unit body to balance the need for physical strength of the tissue/electrode fixation unit interface and comfort for the user. That is, the bending radii and bending angles can be tailored to the specific site of interest. The preferred cross sections of the electrode fixation unit body are ranging from ø1 mm to ø6 mm, although not necessarily being circular. Sections of the electrode fixation unit body having larger circumference, i.e. up to 10 mm, could be optional where a large charge injection is important for the application. The preferred shaft lengths are from 10 mm to 40 mm, and should be anatomically feasible. The size of the electrode fixation unit body follows its dimension relative to the size of patch electrode, for up to 100 mm length. If longer distances of fixation are necessary, application of additional electrode fixation units are preferred. The curvature of the electrode fixation unit determines the depth of the electrode fixation unit into the tissue. The requirement for this depth can vary depending on the local tissue at the site of stimulation, taking into account among other things the length of the electrode fixation unit body, the cross section etc., and the anatomical location of stimulation. If the electrode fixation unit is too small, also relative to the patch electrode, the quality of the fixation will drop, with subsequent increased risk of compromised electrode/tissue interface e.g. loss of function.

Figure 4:
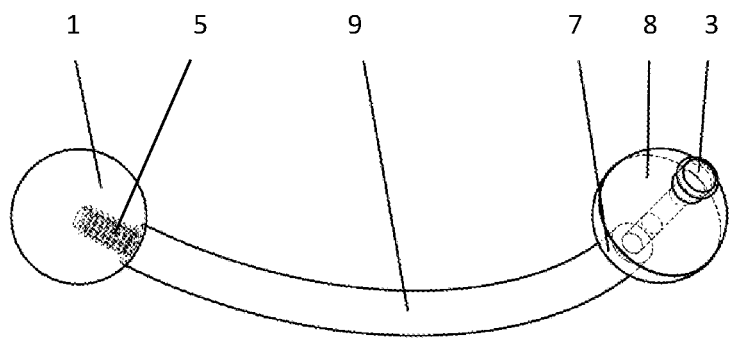
FIG. 4, illustrates a smoothly bended embodiment of the electrode fixation unit body with one end termination attached using threads and one end termination magnetically attached. The latter end termination allows for electrical connection via a connector and lead to a pulse generator.

FIG. 2, FIG. 3 and FIG. 4 are representing various shapes of the electrode fixation unit body (2 or 2 and 6). Further designs could include bended and coiled wires constituting the electrode fixation unit body, providing additional means of fixation into the tissue. Similarly, sharper bended electrode fixation unit body, multi-axis curved electrode fixation unit body designs are means to increase tissue fixation features.

FIG. 4 shows an electrode fixation unit body design (2) utilizing magnetic end termination support for the electrical connected end termination, consisting of an isolating or conducting lower section (7), and isolating upper section (8), and the connector detail (3) for the lead connection. The isolating materials of the end termination/s (7, 8), when designed not to be part of the electrode interface, can comprise PEEK, fluorinated materials, ceramics or similar biocompatible materials. The outer surface of the electrode fixation unit (2) becomes the electrode interface to the nervous tissue. When the lower section (7) of the end termination shall be part of the electrode interface, this part is then design utilizing 316L or precious metals suitable for the application. Thus, the electrode fixation unit body and/or the at least one end termination constitutes an electrical stimulating electrode.

Figure 5:
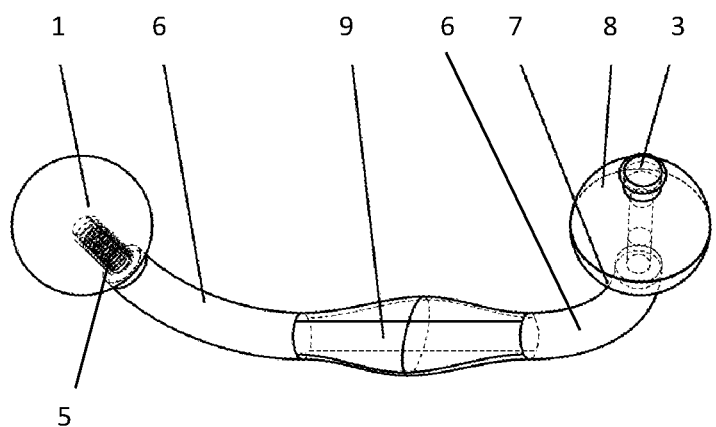
FIG. 5, illustrates an electrode fixation unit with an integrated dedicated stimulating electrode in a monopolar configuration, with at least one end termination having integrated connection details.

FIG. 5 represents an electrode fixation unit body with an integrated stimulation electrode (9) designed in a monopolar configuration. Miniaturization of the active part of the electrodes (9) is limited by the charge storage capacity and impedance of currently applied materials. A monopolar configuration maximizes the optional area relative to the shaft length and cross section of the electrode fixation unit body. Larger charge input may thus require longer electrode fixation unit body designs to obtain larger electrode surfaces (9). The isolating material (6), if any applied in the given design, should be biocompatible or bio-inert, of which PEEK or ceramics are ideal. Other materials could include fluorinated based materials. Thus, the electrode fixation unit body has sections (6) that are intended to be not electrically conductive, hence isolating the stimulating electrode section (9), hindering charge to be directed away from the targeted tissue to be stimulated.

Figure 6:
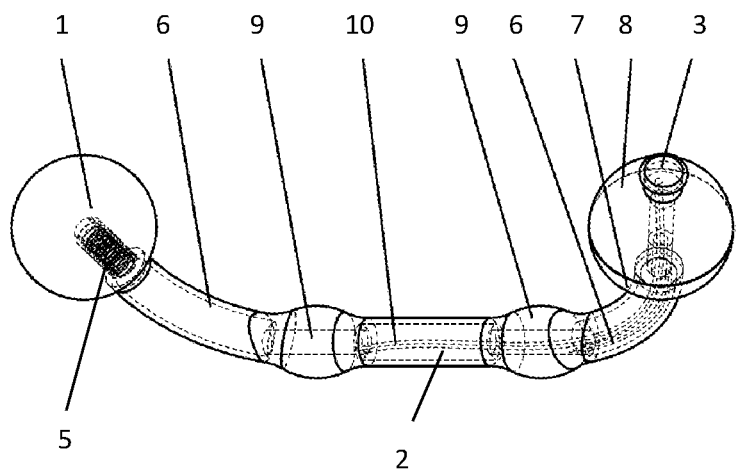
FIG. 6, illustrates an electrode fixation unit with dual integrated stimulating electrodes as a bipolar configuration.

FIG. 6 represents an electrode fixation unit body based fixture design with doubled integrated stimulation electrodes (9) into a bipolar configuration. Tri-polar, quadrupolar or 5-polar electrode concepts could also prove to be relevant options in some applications, although these designs are not included in the illustrations. The shape of the stimulating electrode areas, are of limited importance but should be smooth enough to allow insertion and prevent sharp edges that may become irritant or even unsafe in the formed channel in the tissue. The electrode areas shall be balanced with the load of charge to be injected, the electrode material chosen, and frequency of use of the application applied. A feature for electrical contact is shown as a click-on stud (3), but other designs are also relevant, utilizing, spring loads or magnetism etc. as e.g. shown in FIG. 9. The shape of the electrode fixation unit body can vary in order to allow the stimulating electrodes to be positioned in close contact with the tissue targeted for the charge injection. The depth of the electrode into the tissue is ideally between 2 and 5 mm, but further depth, may be required in some cases, where the excitable tissue is found further profound. For this reason, the bending sections (6) should be tailored to the site of interest. The clinical success of electrical stimulation-based systems depends among other things on the ability of the electrode contact to consistently provide safe levels of stimulation to the target component of the nervous system. Exceeding the limit for safe charge injection may cause electrode degradation and/or irreversible tissue damage resulting in loss of clinical efficacy and the electrode becoming unsafe. To mitigate the problems associated with reduced physical size, advanced biomaterials and precious materials will be used to ensure longevity. The electrode contact/s (9) is the electrochemically active area/s of the electrode where charge transfer occurs during stimulation. The electrode contact is supposed to be in close proximity of the target nerve to obtain low stimulation thresholds. Ideally, the electrode contact/s should have good chemical stability, high charge injection capacity, low electrical impedance, and should remain inserted in the tissue as a compliant material causing low degree of inflammation. Electrical connection (10) to the electrode contacts (9), should ideally run inside the electrode fixation unit body (2), here illustrated as wired connections (10). The internal wiring (10) can also be obtained by the structural parts of the electrodes themselves, or by partially coating of for instance a ceramic electrode fixation unit body. In this manner, simplification of assembly of the electrode fixation unit is obtained. For the positioning of the electrode fixation unit, at least one end termination shall be detachable (1), or a separable electrode fixation unit body should be used, as presented in FIG. 9.

Figure 7:
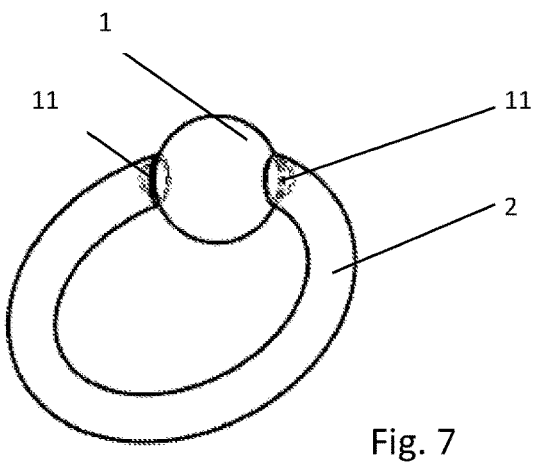
FIG. 7 and FIG. 8, illustrates examples of electrode fixation units having circular electrode fixation unit body shapes.

FIG. 7 illustrates an example of an electrode fixation unit having a closed-loop electrode fixation unit body shape, here presented as a circular electrode fixation unit body shape. The end termination (1) is formed by use of one end termination element, utilizing spring loaded end termination member (11) arranged into carved features in the electrode fixation unit body (2). The electrode fixation unit body need not be circular, and need not have a shape identical to the electrode fixation unit body onto which it is arranged. However, it should have a smooth surface and overall structure for at least the part positioned or arranged inside the formed channel in the tissue. The end termination element could include a structural element providing support on the skin-level, and thus hindering the electrode fixation unit to rotate within the formed channel it is arranged during its intended use.

Figure 8:
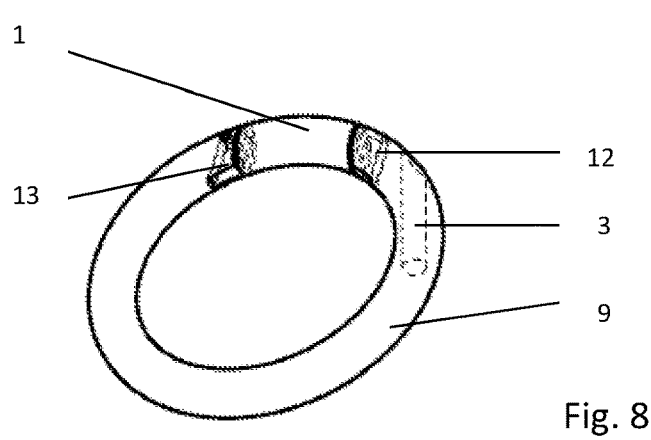

FIG. 8 illustrates examples of electrode fixation units having a closed-loop electrode fixation unit body shape (2), where an end termination (1) is provided through means of a hinged (12) end termination member (1). This could as well be provided in a double hinged design, providing a flexible opening for ease of insertion into the formed channel in the tissue. The direction of hinge-operation is not crucial for its function, but a sort of lock (13), here exemplified as a click-in feature. The hinged element (1) could additionally be made from a ductile formable material, where nitinol includes preferable features, and thus needs not form a closed endless loop, but overlapping or with a short enough distance kept between ends formed, which will have a satisfactory interlocking function. The electrode fixation unit body need not be circular, but should have a smooth surface and structure for at least the part arranged inside the formed channel in the tissue, and can prevent rotational movement if this part flattened/non-circular.

Figure 9:
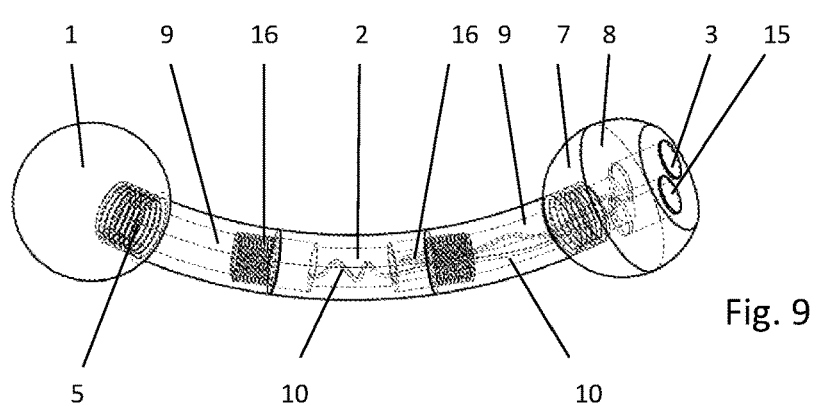
FIG. 9, shows a detailed version of the electrode presented in of FIG. 6, with an electrode fixation unit body in a separable design

FIG. 9 shows a separable version of the electrode fixation unit presented in FIG. 6. The separable electrode fixation unit body design, consisting of two electrodes parts (9) and an isolating part (14), all allowing to be dismantled by use of threaded assembly elements (16) is advantageous for the manufacturing processes. The end termination threaded details could as well be oppositely directed, i.e. having the thread sitting inside the electrode (9), rather than inside the end termination (1), or the lower section (7) in the connector end termination. The assembly element (16) could additionally be formed by means of frictional interference fit.

The mid-section (14) consists of an isolating member, and two conducting assembly members (9) onto which internal wires are connected and electrodes are mounted.

Vice versa, the assembly will form a monopolar electrode fixation unit design. The electrical wires (10) are distributed internally within the midsection member (14) and through an electrode member (9), onto which a connector end termination is arranged, having features (7, 8, 3, 15) forming a connector. The opposite end termination (1) as well as the electrode member it is attached to (9) can be repeatedly dismantled from the electrode fixation unit, as well as assembled onto it.

Figure 10:
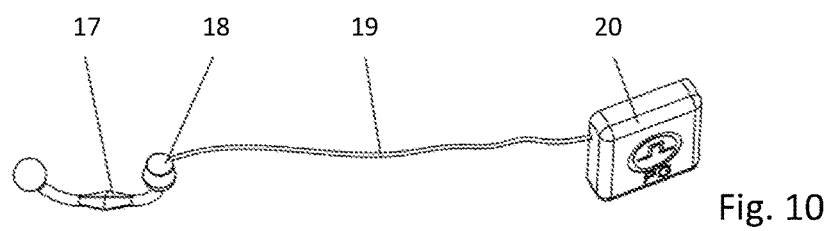
FIG. 10, illustrates an example of the entire system.

FIG. 10 shows an example of an entire electrical stimulation system, represented by the electrode fixation unit (17) of FIG. 5. The lead (19) is detachable and is designed to release connection (18) at a predetermined force, the preferred method of connection being magnetically support. A similar connection can be arranged on the pulse generator (20). The lead shall hold at least the corresponding number of wires as the electrode fixation unit holds electrodes, and hence any of the previous systems illustrated in FIG. 1 to FIG. 9 could constitute the electrode fixation unit (17) as shown in FIG. 10.

The invention claimed is:

1. A system for electrical stimulation of nerves of a living being, comprising:
   an electrode fixation unit configured to be placed in a superficially formed channel in the skin, and specially adapted for providing suitable fixation of at least one electrode, wherein the electrode is configured to be placed in close proximity of a portion of a nerve of the living being, the at least one electrode being placed and configured to conduct current directly into the tissue of the formed channel to electrically stimulate nerves, the at least one electrode attached to the electrode fixation unit, and a pulse generator configured to provide a sequence of electrical pulses to the at least one electrode in order to achieve electrical stimulation of the nerve, wherein:
   the electrode fixation unit has a first end and a second end;
   the first end of the electrode fixation unit is configured to protrude out of the first end of the formed channel and the second end of the electrode fixation unit is configured to protrude out of the second end of the formed channel;
   an electrode fixation unit body forms the structure of the electrode fixation unit, the electrode fixation unit body constituting the fixation member onto which the at least one electrode is arranged or included;
   at least one end termination member, configured to be repeatedly non-destructively dismantled from and reassembled to the electrode fixation unit body, is configured to provide a stop for movement of the electrode fixation unit body in at least one direction within the formed channel, wherein the at least one end termination is positioned outside at least one of the first or second end of the formed channel, providing a mechanically interlocking mechanism by means of geometry of the end termination for the electrode fixation unit when the electrode fixation unit is arranged in the formed channel.

2. The electrode fixation unit according to claim 1, wherein the at least one end termination member is arranged on the electrode fixation unit body as a hinge or ductile formable structure member.

3. The electrode fixation unit according to claim 1, wherein the electrode fixation unit is configured to repeatedly be non-destructively dismantled into at least two elements and reassembled, once arranged in the formed channel.

4. The electrode fixation unit according to claim 1, wherein the electrode fixation unit body is solid-, or hollow-tubular-formed and the cross section is having a triangular, squared or multiple angled cross section until substantially being circular or elliptical formed with even or uneven sized sides and/or with straight or curved sides and wherein the electrode fixation unit in the longitudinal direction can travel in a straight or bended or curved or spiral or meandering or a combination of said travel form directions.

5. The electrode fixation unit according to claim 1, wherein the cross section of the electrode fixation unit is within the range of one millimeter to ten millimeters.

6. The electrode fixation unit according to claim 1, wherein the shaft length of the electrode fixation unit is within the range of ten to forty millimeters.

7. The electrode fixation unit according to claim 1, wherein the curvature of the fixation unit is formed from straight to complete enclosed designs and wherein the said curvature need not be constant.

8. The electrode fixation unit according to claim 1, further comprising a biocompatible electrical conductible material comprising at least one of titanium, medical grade stainless steel, platinum, platinum/iridium, medical grade metals and other precious metal alloys suitable for electrical stimulation; and
   a biocompatible electrical isolating material comprising at least one of silicone, polyurethane, PTFE or PEEK or ceramics and/or comprises a flexible or resilient material.

9. The electrode fixation unit according to claim 1, further comprising biocompatible thermoplastic materials comprising at least one of Polyether-ketone based materials, HD-PE, PP, PET, Fluorinated polymer materials, or other sterilizable materials suitable for permanent contact through the skin of the patient.

10. The electrode fixation unit according to claim 1, wherein the fixation unit or the electrode part are coated with precious metal alloys, titanium nitride or diamond like carbon.

11. The electrode fixation unit according to claim 1, wherein the electrode fixation unit allows to be dismantled in some position on the electrode fixation unit body.

12. The electrode fixation unit according to claim 1, wherein the electrode fixation unit constitutes the at least one electrode.

13. The electrode fixation unit according to claim 1, wherein the electrode fixation unit is electrically conductible all over and serves as an electrode itself and is configured to provide electrical stimulation from the entire surface of the electrode fixation unit at the surface wherein the electrode fixation unit is in contact with tissue.

14. The electrode fixation unit according to claim 1, wherein the electrode fixation unit body is partly made of an electrical isolating material and having electrical electrically conductible sections which serve as electrodes.

15. The electrode fixation unit according to claim 1, comprising at least one detachable electrical connection providing the stimulation signal from a pulse generator to the at least one applied electrode.

16. The electrode fixation unit according to claim 1, comprising a patch member wherein at least one of the first and/or the second ends of the electrode fixation unit are adapted to form at least one point for connecting and supporting said patch member in position on the skin, or wherein the patch member is forming a bridge between said first and second ends of the fixation unit.

17. A system having the electrode fixation unit according to claim 1, wherein the pulse generator is arranged in, on or with the electrode fixation unit or in, on or with a patch member.

18. The system according to claim 17, wherein the pulse generator is connected to the electrode fixation unit via a detachable wired connection.

19. The system according to claim 17, comprising a wired electrical connection between the at least one electrode and the pulse generator and further comprising a connector configured for releasing the wired electrical connection to the pulse generator when a preconfigured pull force is exceeded.

20. The system according to claim 17, comprising a second electrode arranged on the electrode fixation unit, on the patch member or with the pulse generator serving as a counter electrode for the at least one electrode arranged on the electrode fixation unit or on the patch member.

* * * * *